US006589452B2

(12) United States Patent
Asher et al.

(10) Patent No.: US 6,589,452 B2
(45) Date of Patent: Jul. 8, 2003

(54) PHOTOCHEMICALLY CONTROLLED PHOTONIC CRYSTAL DIFFRACTION

(75) Inventors: Sanford A. Asher, Pittsburgh, PA (US); Marta Kamenjicki, Delmont, PA (US); Igor K. Lednev, Pittsburgh, PA (US); Viktor Meier, Freiburg (DE)

(73) Assignee: University of Pittsburgh, Pittsburgh, PA (US)

( * ) Notice: Subject to any disclaimer, the term of this patent is extended or adjusted under 35 U.S.C. 154(b) by 141 days.

(21) Appl. No.: 09/791,192

(22) Filed: Feb. 23, 2001

(65) Prior Publication Data

US 2002/0008229 A1 Jan. 24, 2002

Related U.S. Application Data

(60) Provisional application No. 60/184,499, filed on Feb. 23, 2000.

(51) Int. Cl.[7] .............................. G03C 1/00; G02B 5/23; G02B 5/08

(52) U.S. Cl. ....................... 252/600; 252/586; 359/886; 359/290; 359/296

(58) Field of Search ............................... 252/586, 600; 359/886, 290, 296

(56) References Cited

U.S. PATENT DOCUMENTS

| | | | |
|---|---|---|---|
| 3,620,597 A | 11/1971 | Schwartz et al. | 350/160 |
| 4,268,413 A | 5/1981 | Dabisch | 252/408 |
| 4,548,473 A | 10/1985 | Lo et al. | 350/311 |
| 4,627,689 A | 12/1986 | Asher | 350/362 |
| 4,632,517 A | 12/1986 | Asher | 350/362 |
| 4,648,686 A | 3/1987 | Segawa | 350/96.13 |
| 4,720,355 A | 1/1988 | DeMartino | 252/582 |
| 4,803,688 A * | 2/1989 | Lawandy | 359/296 |
| 4,828,362 A | 5/1989 | Skinner et al. | 350/320 |
| 4,832,466 A | 5/1989 | Nichimura et al. | 350/354 |
| 4,938,557 A | 7/1990 | Blow | 350/96.15 |
| 5,231,140 A | 7/1993 | Kilburg et al. | |

(List continued on next page.)

FOREIGN PATENT DOCUMENTS

| | | |
|---|---|---|
| EP | 0433901 | 6/1991 |
| EP | 0514750 | 11/1992 |
| JP | 5165142 | 6/1993 |
| JP | 5320227 | 12/1993 |
| WO | 9219654 | 11/1992 |
| WO | 9302384 | 2/1993 |
| WO | 9404952 | 3/1994 |
| WO | 9819787 | 5/1998 |
| WO | 00/47167 | * 8/2000 |

OTHER PUBLICATIONS

Pan G., Tse A.S., Kasavamoorthy R., Asher S.A.; "Synthesis of Highly Fluorinated Monodisperse Collids for Low Refractive Index Crystalline Colloidal Arrays" *J.Am. Chem. Soc.* 120:6518–6524, (1998).

(List continued on next page.)

*Primary Examiner*—Philip Tucker
(74) *Attorney, Agent, or Firm*—Baker Botts L.L.P.

(57) ABSTRACT

The present invention is related to photonic crystal devices that comprise novel mesoscopic periodic materials which comprise polymerized crystalline colloidal arrays (CCA) and at least one photosensitive component. Preferably, the photosensitive component is a photochromic molecule and more preferably the component is an azobenzene derivative. Methods for making these devices are also disclosed. The devices of the present invention are useful in many applications including, for example, optical switches, display devices and memory storage devices. The devices of the present invention permit the possibility to write with ultraviolet light and erase with visible light. In addition, the present invention is related to a functionalized polymerized crystalline colloidal array which preferably comprises reactive epoxide groups. The present invention is further directed to a photosensitive polymerized crystalline colloidal array.

45 Claims, 3 Drawing Sheets

U.S. PATENT DOCUMENTS

| | | | |
|---|---|---|---|
| 5,266,238 A | 11/1993 | Haacke et al. | 252/582 |
| 5,281,370 A | 1/1994 | Asher et al. | 264/1.1 |
| 5,330,685 A | 7/1994 | Panzer et al. | 252/582 |
| 5,338,492 A | 8/1994 | Panzer et al. | 252/582 |
| 5,342,552 A | 8/1994 | Panzer et al. | 252/582 |
| 5,368,781 A | 11/1994 | Haacke et al. | 252/582 |
| 5,452,123 A | 9/1995 | Asher et al. | 359/296 |
| 5,462,698 A | 10/1995 | Kobayakawa et al. | |
| 5,737,102 A * | 4/1998 | Asher | 359/296 |
| 5,759,447 A | 6/1998 | Efron et al. | |
| 5,914,193 A | 6/1999 | Ono et al. | |
| 6,014,246 A | 1/2000 | Asher et al. | 359/288 |
| 6,092,530 A | 7/2000 | Weissman et al. | 128/899 |
| 6,094,273 A | 7/2000 | Asher et al. | 356/415 |
| 6,165,389 A | 12/2000 | Asher et al. | 252/582 |
| 6,187,599 B1 * | 2/2001 | Asher et al. | 252/582 |
| 2002/0031841 A1 * | 3/2002 | Asher | 359/886 |
| 2002/0118435 A1 * | 8/2002 | Foulger et al. | 359/265 |

OTHER PUBLICATIONS

Reese C.E., Guerrero C.D., Weissman J.M., Lee K., Asher S.A.; "Synthesis of Highly Charged, Monodisperse Polystyrene Colloidal Particles for the Fabrication of Photonic Crystals", *Journal of Colloidand Interface Science* 232: 78–80 (2000).

Vanderhoff et al., "Well–Characterized Monodisperse Latexes" (*Journal of Colloid and Interface Science,* 28:336–337 (1968)).

* cited by examiner

PHOTOCHEMICALLY CONTROLLED PHOTONIC CRYSTAL DIFFRACTION

Priority is claimed under 35 U.S.C. §119(e) to U.S. Provisional Patent Application Ser. No. 60/184,499 which was filed Feb. 23, 2000.

This invention was made with government support under ONR Grant # N00014-94-1-0592 and DARPA Grant # DAAD16-99-C-1036. Therefore, the government has certain rights in the invention.

BACKGROUND OF THE INVENTION

Charged colloidal particles, when suspended in water, form a stable dispersion due to interparticle coulomb repulsion forces. The property of structural ordering in such dispersions has been exploited in making devices such as narrow band optical rejection filters. The ordering phenomena in such colloidal suspensions has been useful in spectroscopy and Bragg diffraction techniques. See, for example, U.S. Pat. No. 4,627,689. It has been found that mesoscopic, crystalline structures can have many practical applications as optical filters in military, space, medical and research uses. In many such instances, it is necessary or desirable to filter narrow bands of selected wavelengths from a broader spectrum of incident radiation.

U.S. Pat. No. 4,627,689 of Asher discloses a linear crystalline colloidal narrow band radiation filter which is made by forming a highly ordered crystalline colloidal structure within a container. The crystalline colloidal structure is formed by dispersing the ionized particles, for example, polystyrene particles, within an appropriate solvent.

A related disclosure was made in U.S. Pat. No. 4,632,517 of Asher which discloses another crystalline colloidal narrow band radiation filter application. U.S. Pat. No. 4,632,517 forms the basis for a mechanically simple and highly efficient monochromator. It has application in improved systems for investigating Raman or emission spectra of selected sample materials. Both of the aforementioned patents disclose structures that can be used to diffract a narrow band of radiation from a broader band of radiation.

A solid filter and method of making a solid filter from an ordered dispersion of particles within a medium is disclosed in U.S. Pat. No. 5,281,370 of Asher. That patent discloses a filter which is capable of Bragg diffracting narrow bands of radiation. It is a solid filter which has many practical applications.

An optical filter was also disclosed in U.S. Pat. No. 4,548,473. The filter comprises a first substance substantially transparent to light within a select frequency range and having a first index of refraction. The filter also includes a second substance which has at least one resonance frequency within the first frequency range and a second index of refraction which is substantially the same as the first index of refraction at all of the frequencies within the first frequency range except for frequencies near the resonance frequency. This device is based upon resonance scattering by a disordered sample. The device is only a passive device meaning that the index of refraction is not considered to depend upon the incident intensity or time.

U.S. Pat. No. 3,620,597 discloses a device which is capable of acting as a nonlinear absorber of substantially all radiant energy in excess of a predetermined intensity. The mechanism utilized by the device is distinct from that of the present invention.

U.S. Pat. No. 4,832,466 is directed to an optical element including a modulating liquid layer composed of a solvent containing a soluble polymer. The device requires polymers to precipitate from solution due to temperature changes. This is not required by the present invention.

U.S. Pat. No. 4,648,686 discloses an optical switch array which utilizes the temperature dependent characteristics of the index of refraction of a crystalline material, however, the device is limited to being used for switching in a waveguide. Other switches for use in waveguides were disclosed in U.S. Pat. Nos. 4,828,362 and 4,938,557.

U.S. Pat. No. 4,268,413 provides devices having the property of reversibly variable temperature-light absorbance. The device is said to be usable in temperature-measuring devices, slippery ice warning devices and the like.

U.S. Pat. No. 5,452,123 discloses a nonlinear optical device and method for making the same. The method includes making a solid or crystalline colloidal ordered dispersion of charged particles within a medium and introducing into the particles or the medium a radiation responsive component which, when impinged with radiation at a critical intensity, causes a change in the refractive index of the particles in either the ordered dispersion, the medium or both.

U.S. Pat. Nos. 5,368,781 and 5,266,238 are directed to tunable, narrow band radiation filters comprising a crystalline colloidal array of charged particles fixed in a hydrogel film. Methods for filtering incident radiation using these filters are also disclosed.

U.S. Pat. No. 4,720,355 is directed to a non-linear optical medium having a "host" thermoplastic polymer which contains a "guest" organic component; the organic component has a charge asymmetric electronic stricture and exhibits non-linear optical response.

U.S. Pat. Nos. 5,330,685, 5,338,492 and 5,342,552 all provide narrow band radiation filters comprising a CCA of charged particles in a polymeric hydrogel.

U.S. Pat. Nos. 6,165,389; 6; 6,094,273 and 6,014,246 are directed to devices which comprise mesoscopically periodic materials that combine crystalline colloidal array self-assembly with the temperature and/or pressure induced volume phase transitions of various materials. The devices are useful as optical switches, optical limiters, optical filters, display devices, and processing elements as well as membrane filters.

Despite the above, there remains a need for devices which permit a simplified means of writing and erasing data. Such devices are capable of a photoreversible shift in diffracted light and are useful as optical switching devices. The devices of the present invention fulfill this need by permitting the possibility to write with ultraviolet light and erase with visible light.

SUMMARY OF THE INVENTION

The present invention provides devices useful, inter alia, as optical switches, display devices and memory storage devices that are capable of a photoreversible shift in diffracted light.

The devices comprise novel mesoscopically periodic materials which comprise crystalline colloidal arrays (CCA) polymerized in a hydrogel and at least one photosensitive component attached to the polymerized CCA. Preferably, the photosensitive component is a photochromic molecule, for example, a derivative of azobenzene. The periodic materials comprising these photoswitchable CCA have a periodicity that can be reversibly switched with ultraviolet (UV)

and visible light. The result is a polymerized CCA (PCCA) which is photoresponsive and which undergoes a continuous volume change upon irradiation. The devices additionally permit the possibility to write with ultraviolet light and erase with visible light, or vice versa.

The present invention also relates to a new method for functionalizing PCCA. In addition, the present invention relates to a new azobenzene derivative which has improved water solubility and which maintains its photochemical properties. The azobenzene derivative (Formula VII) of the present invention may be prepared according to the method described in Example 4 below.

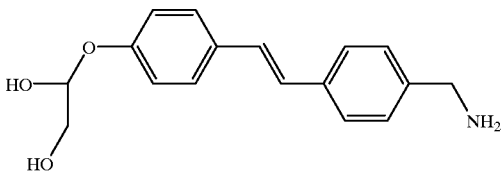

(VII)

The azobenzene derivative of the present invention has improved water solubility characteristics than non-derivatized azobenzene. In addition, it retains similar photochemical properties as non-derivatized azobenzene.

Methods for making the devices of the present invention are also provided. Generally these methods involve creating a crystalline colloidal array, using highly charged monodisperse colloidal particles that self-assemble into crystalline colloidal arrays (CCA), and polymerizing a hydrogel network around the CCAs to form PCCAs which permanently locks in the ordering of the CCAs.

In one embodiment of the invention, the PCCA is functionalized such that the photosensitive component may be attached to a PCCA. In a particularly preferred embodiment of the invention, the PCCA is functionalized by the addition of glycidyl methacrylate to introduce reactive epoxide groups. Attachment of a photosensitive component to the reactive PCCA is accomplished through the reaction of reactive groups of the component with the epoxide groups of the PCCA. For example, the epoxide groups inside the hydrogel may be reacted with primary amino groups on an azobenzene derivative. The resultant photosensitive PCCA comprising at least one photosensitive component can undergo a reversible change in volume in response to irradiation. Other photosensitive components that undergo a change in volume in response to irradiation may also be used, such as, inter alia, spiropyranes, spiroxazines, fulgides, diarylethenes, benzothiazolium styryl dyes, and triphenylmethane derivatives.

The devices of this invention can form the basis for mechanically simple and highly efficient optical switches, display devices, and memory storage devices which are useful for computer applications. Overall, the devices can be used with any product in which the disclosed characteristics are desirable.

It is an object of the present invention to provide an optical switching device which can operate to Bragg diffract certain wavelength bands of incident light.

It is a further object of the present invention to provide an optical switching device that undergoes a reversible change in volume upon irradiation.

It is another object of the invention to provide a device that functions as a display device.

In addition, it is an object of the present invention to provide a device that functions as a memory storage device.

It is yet a further object of the present invention to provide a device that can write and erase. For example, but not by way of limitation, the devices of the present invention can write with UV light and erase with visible light.

BRIEF DESCRIPTION OF THE DRAWINGS

The invention may be better understood in reference to the attached drawings in which.

DETAILED DESCRIPTION

Figure 1:
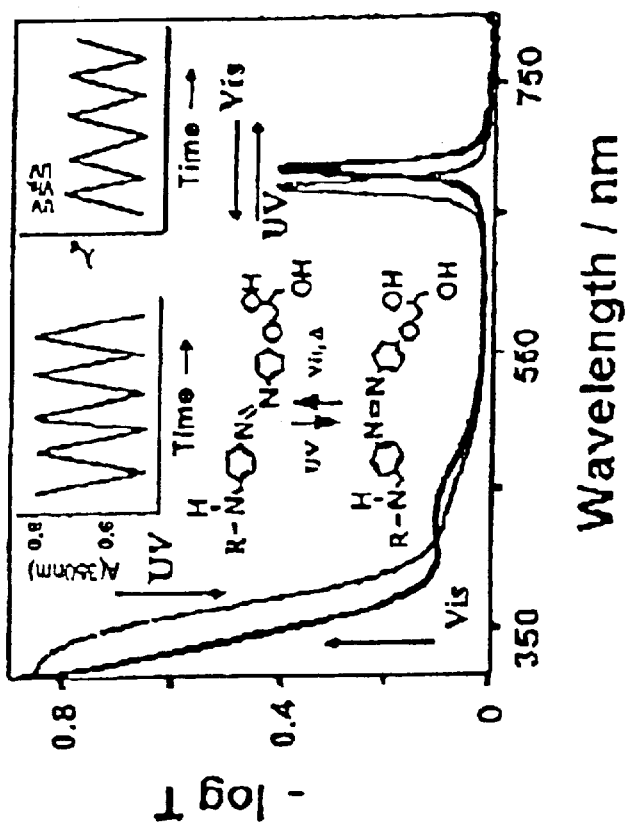
FIG. 1 is a graph demonstrating the photoresponsiveness of an azobenzene functionalized PCCA to irradiation with UV and visible light. The observed diffraction behavior is reversible and the successive irradiation with UV and visible light can be repeated many times. The gel was irradiated with UV light (365 nm, $Ar^+$ laser) and the absorption spectra were measured. The gel was then irradiated with visible light (488 nm, $Ar^+$ laser) and absorption spectra measured again. We recorded the spectra using a UV-visible-near IR spectrophotometer (Perkin-Elmer λ-9, Oak Ridge, Tenn.).

The present invention is directed to novel devices and methods of making the devices. The present invention is further directed to methods of using these devices as optical switches, display devices and memory storage devices.

"Optical switch", as referred to herein, is a device that may be "switched" off or on in response to a stimulus such as irradiation. The term "band" of wavelengths will be understood by those in the art to refer to a span of wavelengths. This band can be narrow, with a width of less than one nanometer, or broad, encompassing many nanometers.

The devices of the present invention generally comprise an ordered crystalline colloidal array (CCA) of ionized colloidal particles in an appropriate solvent and embedded in a hydrogel matrix. See generally U.S. Pat. Nos. 6,165,389; 6,092,530; 6,094,273 and 6,014,246 of Asher et al., incorporated herein by reference.

The material used to form the matrix, according to one embodiment of the present invention, includes a crystalline colloidal array (CCA) surrounded by the polyacrylamide network. The CCA can be formed using any highly charged particles (as long as they are uniform in size and surface charge) in a suitable solvents. In a particular embodiment an aqueous solution of "fluorinated particles" composed of poly(1H,1H-heptafluorobutyl methacrylate) and polystyrene particles was used.

Monodisperse, highly charged colloidal particles dispersed in very low ionic strength liquid media self-assemble due to electrostatic repulsion to form CCA. These ordered structures are either body-centered cubic (BCC) or face-centered cubic (FCC) arrays with lattice constants in the mesoscale range (50–500 nanometers (nm)). Just as atomic crystals diffract x-rays meeting the Bragg condition, CCA diffract ultraviolet (UV), visible and near infrared (IR) light. CCA can be prepared as macroscopically ordered arrays from non-close packed spheres. Such arrays exhibit highly efficient Bragg diffraction; nearly all light meeting the Bragg condition is diffracted, while adjacent spectral regions not meeting the Bragg conditions will freely transmit. "Non-close packed spheres" refers to an ordering wherein the spheres are spaced by some distance from each other.

The Bragg diffraction law is represented by the following formula:

$$m\lambda = 2nd \sin \theta;$$

where m is the order of diffraction, $\lambda$ is the wavelength of incident light, n is the suspension refractive index, d is the interplanar spacing, and $\theta$ is the angle between the incident light and the crystal planes.

The particles used to create the CCA can be any particle selected from among colloidal polystyrenes, polymethylmethacrylates, silicon dioxides, aluminum oxides, polytetrafluoroethylenes and any other suitable materials which are generally uniform in size, surface charge and show no absorption or diffraction in the spectral regions needed for photoswitching. The particles are chosen for their properties as desired for the particular application. The particles preferably have a diameter between about 50 and 500 nm and may be either synthesized as discussed below or obtained commercially.

In a particular embodiment of the invention, 140 nm fluorinated colloids and polystyrene colloids were used. Highly charged monodisperse fluorinated colloidal particles of diameter between 50 and 250 nm were synthesized from 1H,1H-heptafluorobutyl methacrylate (FBMA) by free-radical emulsion polymerization ("fluorinated colloids"). These fluorinated colloidal particles have a low refractive index of 1.386. High particle surface charge densities were obtained by minimizing the polymer molecular weight. This synthetic methodology has been described by Pan G., Tse A. S., Kasavamoorthy R., Asher S. A.; *J. Am. Chem. Soc.* 120:6518–6524 (1998). See Example 1 below.

Highly charged monodisperse colloidal polystyrene particles were formed by emulsion polymerization. These spherical colloidal particles were crosslinked with divinyl benzene and functionalized with 1-sodium-1-allyloxy-2-hydroxypropane sulfonate in water. One useful method is described by:Reese C. E., Guerrero C. D., Weissman J. M., Lee K., Asher S. A.; *Journal of Colloid and Interface Science* 232:78–80 (2000). See Example 1 below.

The particles may be purified by any means known in the art. In one preferred embodiment, purification is accomplished by dialysis and/or use of ion exchange resin. Purification helps to ensure self-assembly of the CCA, which generally needs to take place in a very low ionic strength medium. The colloids can be dialyzed against a suitable medium. In a particular embodiment, the colloids were dialyzed against deionized water with the use of dialysis membranes (Spectra/Por. MWCO=50 000) by changing the water daily until the specific conductivity was constant (~1 $\mu$S/cm). Further purification was achieved by shaking the latex with ion-exchange resin. Mixed bed ion-exchange resin (AG 501-X8, 20–50 mesh) was obtained from Bio-Rad (Richmond, Calif.).

The particles may be stored in an ion exchange resin, preferably in a bath of 10% by weight suspension of ion exchange resin such as analytical grade AG501X8 mix bed resin which is commercially available (Bio-Rad, Richmond, Calif.). The ion exchange resin should preferably be cleaned prior to use through a suitable procedure such as that taught by Vanderhoff et al. (*Journal of Colloid and Interface Science,* 28:336–337 (1968)). The suspension showed iridescent color, indicating the formation of a CCA which Bragg diffract light at wavelengths preferably from the near-IR to 270 nm in the UV region.

The concentration of fluorinated or polystyrene CCA particles in the water determines the wavelength the CCA diffracts light. Generally, the higher the particle concentration the shorter the wavelength of the light diffracted.

When synthesizing colloidal particles, any other suitable ionic co-monomers, crosslinkers, surfactants and free-radical initiators can be used, absent compatibility problems. Alternatively, highly charged, monodisperse particles that can be used in accordance with this embodiment are commercially available from Dow Chemical or Polysciences, Inc. Purification of the commercially available particles is also recommended.

A polymerized CCA (PCCA) is made by locking the crystalline colloidal particles inside the hydrogel network. The width and height of the diffraction peak can be easily controlled by choosing colloidal particles of different size and refractive index or by making different thickness PCCA films.

The PCCA of the present invention may comprise reactive groups, for example, reactive epoxide groups. The present invention is also directed to a PCCA having reactive groups, referred to herein as a functionalized PCCA and methods for preparing the same. In one embodiment, the functionalized PCCA is prepared by copolymerizing acrylamide with glycidyl methacrylate in order to introduce reactive epoxide groups into the PCCA. The functionalized C PCCA may be attached through its reactive groups to a photosensitive component to create a photosensitive PCCA which comprises a photosensitive component. The photosensitive component may be covalently attached to the functionalized PCCA. This method is fast, provides good control of the diffraction wavelength, and does not hydrolyze the polymer network (which causes PCCA to swell).

In another embodiment, a functionalized PCCA is prepared by treating the PCCA with a base (such as NaOH) in order to induce hydrolysis of the amide groups inside the polyacrylamide. In this case, carboxylic groups are created, which can be used for further attachment of desired components. For example, a photosensitive component comprising an amine group can be covalently attached to the hydrogel network by using the linker 1-ethyl-3-(3-dimethylaminopropyl)carbodimide (EDC), which is a water soluble coupling agent used to facilitate the formation of amide bonds between a carboxylic groups and amines.

The present invention is also directed to a method for attaching components to a PCCA comprising making a functionalized PCCA which comprises reactive groups, such as, inter alia, reactive epoxide groups and reactive carboxylic groups, and exposing the functionalized PCCA to a component wherein said component reacts with the reactive groups in the PCCA. In one embodiment, the method for attaching components to a PCCA comprises copolymerizing glycidyl methacrylate with acrylamide wherein said copolymerization results in a PCCA having reactive epoxide groups. The method may further comprise exposing the PCCA to a photosensitive component which comprises an amine wherein said component is covalently attached to the PCCA through reaction of the amine with the reactive epoxide groups. The photosensitive component may be a photochromic molecule.

A functionalized PCCA, according to the present invention, was prepared by dissolving glycidyl methacrylate in a CCA water solution containing acrylamide, a crosslinking agent (preferably N,N'-methylenebisacrylamide) and a photoinitiator, such as, but not limited to a non-ionic ultraviolet (UV) initiator (preferably 2,2-diethoxyacetophenone).

Any crosslinking agent may be used. Preferred ratios of crosslinking agent to monomer are about 1:5 to 1:20. Preferred crosslinking agents are N,N'-methylenebisacrylamide and N,N'-methylenebismethacrylamide. Upon polymerization, the crosslinking agents form a crosslinked polymer network which keeps the colloidal array intact. Generally, the more crosslinking agents used the higher the rigidity and lower the responsivity of the hydrogel. Thus, the amount of crosslinker can be altered to control the desired response in the device. Hydrogel films can be formed with retention of the crystalline colloidal array structure when as little as 1 part in 100 parts by weight of the co-monomer mixture is the crosslinking agent. See U.S. Pat. Nos. 6,165,389; 6,092,530; 6,094,273 and 6,014,246, incorporated herein by reference.

The CCA mixture comprising dissolved monomers, crosslinking agent and a photoinitiator was injected into a cell having two quartz plates (made of UV fused silica) and exposed to mercury lamp at a room temperature. Quartz plates can be separated by a parafilm spacer (American National Can™) or DuraSeal™ spacer (Diversified Biotech, Boston, Mass.). See U.S. Pat. Nos. 6,165,389; 6,092,530; 6,094,273 and 6,014,246, incorporated herein by reference.

Any other means known in the art can also be used for polymerization so long as the method chosen for polymerization does not destroy or otherwise disorder the CCA. Upon completion of the polymerization, the plates are removed and a stable PCCA can be washed with nanopure water. Deionized water was obtained from a Nanopure™ System (Barnstead/Thermolyne Co., Dubuque, Iowa). See Example 2.

As will be appreciated by one skilled in the art, the hydrogel can be made from any monomers, including but not limited to acrylamide monomers. Such monomers preferably undergo a volume change when the free energy of mixing is altered.

In a particular embodiment of the invention, an azobenzene derivative, which is modified in order to increase its water solubility, is attached to the reactive PCCA through the reaction of the epoxide groups inside the hydrogel with primary amino groups on the azobenzene derivative. See Example 3. Hereinafter, the functionalized PCCA having azobenzene attached thereto is referred to as "AZO-PCCA". Photosensitive components which do not have a primary amino group that can react with the epoxide groups may also be used in accordance with the present invention. Such components which do not have a primary amino group may be directly copolymerized with acrylamide. Preferably, the photosensitive component which does not have a primary amino group has a terminal vinyl group and may be water soluble and nonionic. For example, spiropyran may be attached to the gel by directly copolymerizing the spiropyran with the acrylamide. The photosensitive components of the present invention may be synthesized by methods well-known in the art.

The present invention is also directed to an azobenzene derivative (Formula VII) which has improved water solubility and methods for preparing the same. See Example 4.

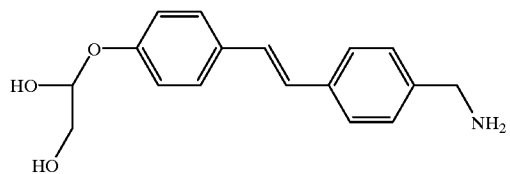

(VII)

Nonlimiting examples of photosensitive components which are suitable in the present invention include azobenzene, spiropyranes, spiroxazines, fulgides, diarylethenes, benzothiazolium styryl dyes, and triphenylmethane derivatives.

The attachment of a photosensitive component, such as azobenzene, to the reactive PCCA results in a photosensitive PCCA. The photosensitive PCCA changes its volume (therefore, changing diffraction wavelength) in response to light. For example, in the dark, the device, which is useful as a photoswitching device, may comprise a photosensitive component in the form of a trans molecule (e.g. a trans azobenzene molecule). Exposure to UV light causes photochemical changes in the photosensitive component, for example, inducing it to form a cis molecule (e.g. a cis-azobenzene molecule). These changes in the photosensitive component may modify the polymer network around CCA. The polymer network may become more hydrophilic, and therefore, more soluble in aqueous medium. As a result, there may be a change in the free energy of mixing inside the gel. When the device is exposed to UV light, an increase in volume may cause an increase in the inter-particle spacing and therefore may red-shift the CCA diffraction. When the device is exposed to visible irradiation, a trans molecule (e.g. trans-azobenzene) may be regenerated. This may result in a reduction in the photosensitive PCCA's volume and may blue-shift the diffraction (see FIGS. 1 and 2). Successive irradiation with UV and visible light results in successive red-shifts and blue-shifts (see FIG. 1 insert).

The ability of the device of the present invention to red-shift and blue-shift, is likely due to the fact that light induces changes in dipole moment and geometrical structure of the photosensitive component. This may cause a change in the free energy of mixing of the system which may result in volume changes. The change in hydrogel volume affects the spacing between colloidal particles and shifts the diffraction wavelength of the device. The amount of the shift is dependent on the amount of irradiation and the PCCA composition.

One embodiment of the present invention is generally directed toward an optical device comprised of a photosensitive PCCA. It is a feature of such an optical device that the diffraction wavelength of photosensitive PCCA can be altered or switched in response to irradiation such that both the swelling and shrinking of the PCCA can be controlled by using different beams of light. See FIG. 1.

The trans-cis photoconversion of individual azobenzene molecules in solution occurs in the picosecond time range. The response time of the AZO-PCCA diffraction shift is controlled by the actinic light power, and is limited by the collective diffusion constant of the hydrogel polymer network. A quantum yield of 0.2 was estimated for one AZO-PCCA, indicating that the photochemical conversion is very efficient. Thus, photoswitching effect can be actuated by a single laser pulse. The photosensitive PCCA of the present invention may operate as a high speed optical switch, in which the diffraction peak red-shifts under UV radiation and blue-shifts under visible irradiation in a time scale range from about picoseconds to about seconds, and more preferably from about nanoseconds to about milliseconds. The ability of the device to write (red-shift) with UV light and erase (blue-shift) with visible light (or vice versa, write with visible and erase with UV light), makes the device of the present invention useful as memory storage device.

The azobenzene derivative of the present invention, as indicated above, is represented by Formula VII.

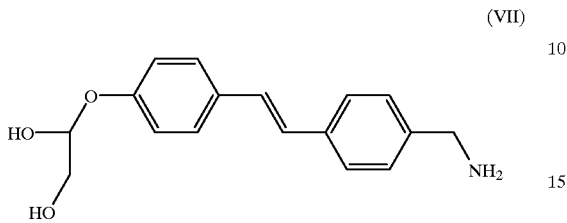
(VII)

Figure 2:
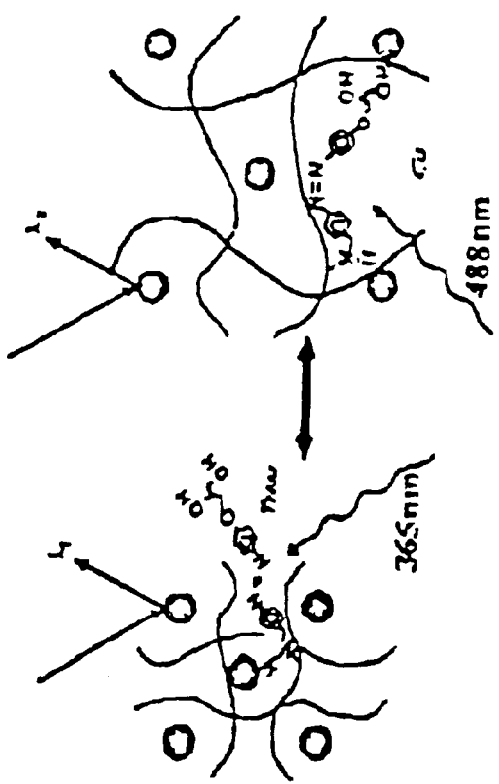
FIG. 2 is a pictorial representation of the switching effect. Exposure to UV light causes isomerization of trans azobenzene, which decreases the hydrophobicity of the polymer network around the CCA. These changes cause a red-shift of diffraction under UV light as the polymer expands. A blue-shift of the diffraction peak is observed under irradiation with visible light.

The azobenzene derivative of the present invention shows very similar photochemical properties as non-derivatized azobenzene. The absorption spectra of the azobenzene derivative of the present invention in the dark shows a strong peak with maximum at 348 nm from $\pi\pi^*$ transition of azo-compounds (mainly trans-azobenzene). In addition, a shoulder arising from the $n\pi^*$ transition is evident at long wavelength side of the $\pi\pi^*$ peak. This peak, due to $n\pi^*$ transition, at 434 nm becomes dominant when a photostationary state under UV irradiation is reached (mainly cis-azobenzene). The intensity of the $n\pi^*$ peak increases as the intensity of the $\pi\pi^*$ band decreases due to the conversion of trans isomer to cis under UV light (FIG. 1). This is a typical behavior of azobenzene-type molecules. The photochemical behavior of a water solution of the azobenzene derivative of the present invention was determined under UV irradiation (365 nm, 20 mW) and irradiation with visible light (488 min, ~50 mW). Under 488 nm irradiation, the trans-isomer is restored and the photostationary state under visible light is very close to the equilibrium state in dark. When the azobenzene derivative was exposed to 365 nm irradiation, kinetic data fitted well to monoexponential function with the characteristic time of ~40 seconds. In addition, thermal relaxation in dark follows monoexponential function with characteristic time of about 10 days at 24° C. Furthermore, the photochemical behavior of the azobenzene derivative of the present invention when covalently attached to the functionalized PCCA of the present invention was close to that of the azobenzene derivative in solution. The retention of the photochemical behavior of the azobenzene derivative when attached to the PCCA may be due to the point of attachment (the reacting amino group) is far from the azobenzene chromophore group which is responsible for its photochemical behavior.

In addition, the present invention is directed to azobenzene intermediates which are represented by Formulas I through VI.

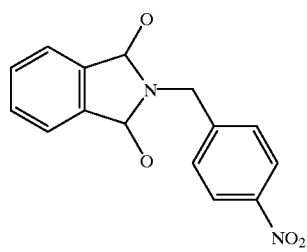
I

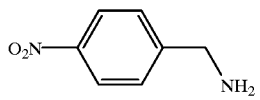
II

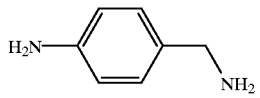
III

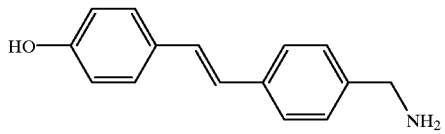
IV

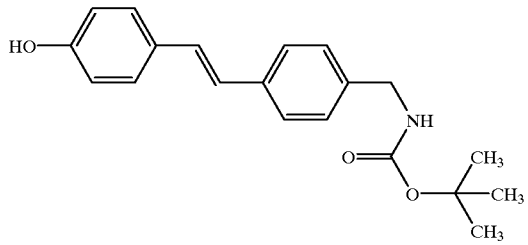
V

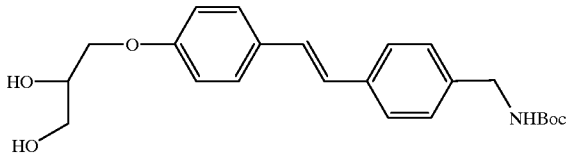
VI

The present invention is also directed to a method for making the azobenzene derivative of the present invention comprising the following steps:

1.

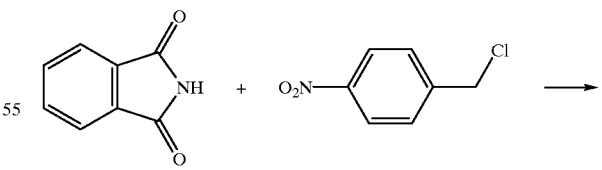

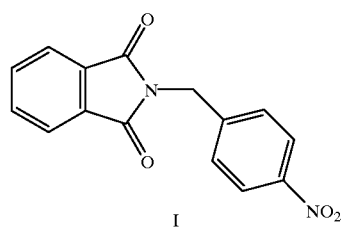
I

-continued

2.

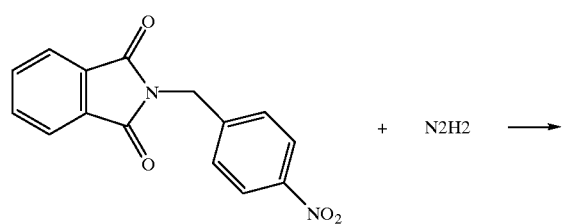

3.

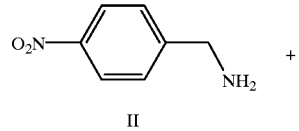

4.

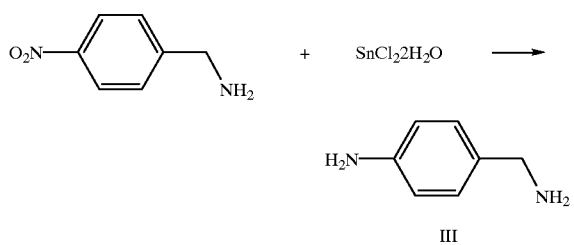

5.

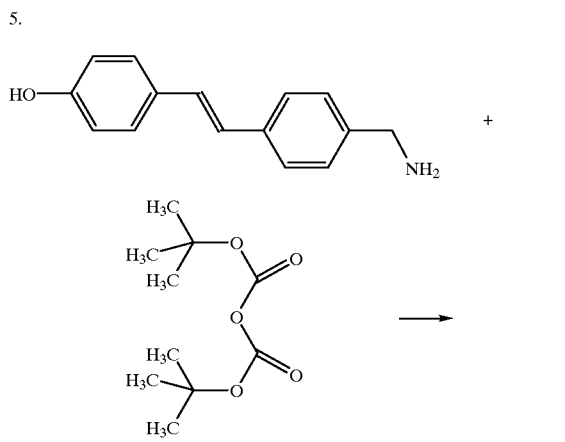

-continued

5.

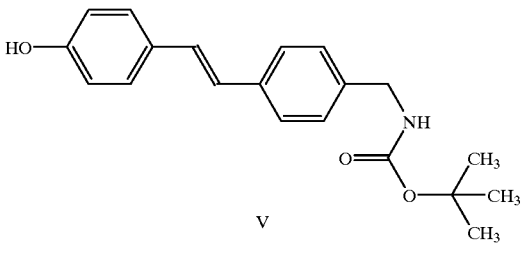

6.

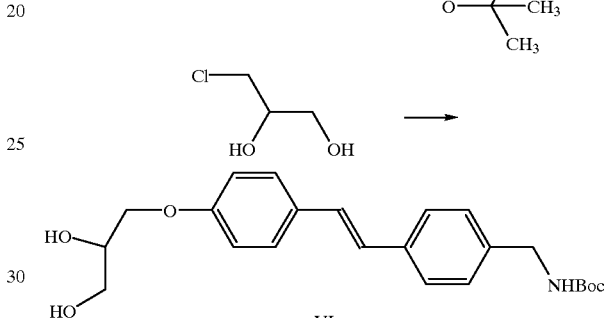

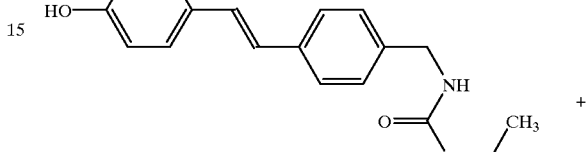

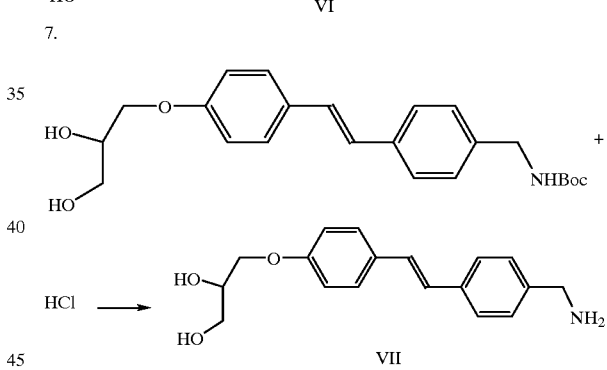

7.

Figure 3:
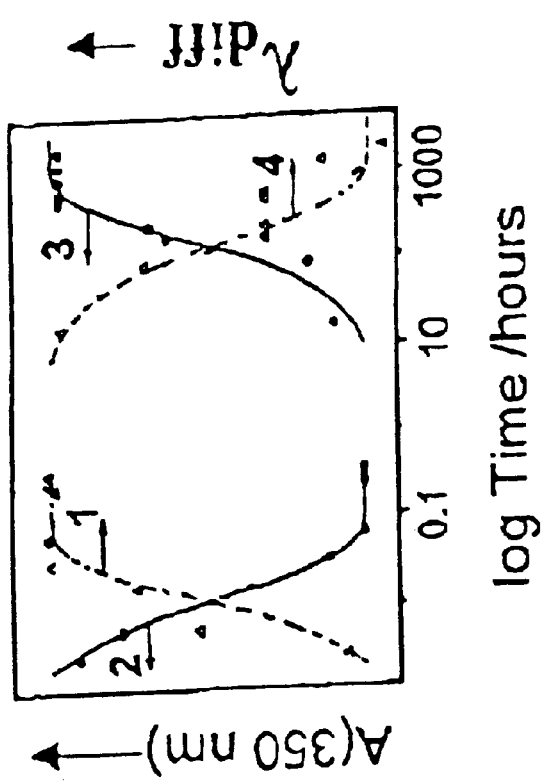
FIG. 3 is a graph showing the characteristic time for UV irradiation and thermal relaxation of the AZO-PCCA. The characteristic time for UV irradiation (trans-cis azobenzene isomerization), which was performed at 365 nm, 10 mW, is ~50 seconds (curve 1 and 2). The response time of the PCCA diffraction shift could be reduced by increasing the actinic light power. In addition, the characteristic time for thermal relaxation (cis-trans azobenzene isomerization), which was performed by placing the AZO-PCCA in the dark, is ~10 days (curve 3 and 4).

FIG. 3 shows that the photoresponse of the AZO-PCCA has the characteristic time of ~50 seconds for the process under low intensity UV irradiation (~10 mW/cm$^2$). The exposure of the AZO-PCCA to visible light (488 nm; ~100 mW) results in a blue-shift of diffraction with a characteristic time of ~3 seconds. The response time of the can be reduced by increasing the actinic light power. The fastest response is limited (1) by the kinetics of isomerization of the photosensitive component, which is in the picosecond range for azobenzene isomerization, and (2) by the relaxation process of the hydrogel.

Thermal relaxation in the dark of the photosensitive component is very slow when it is attached to the functionalized PCCA. For example, AZO-PCCA thermal relaxation at 24° C. was found to be monoexponential with the characteristic time of more than 10 days (see FIG. 3, insert). This time is comparable to the thermal relaxation of the azobenzene derivative in solution.

The response of the photosensitive PCCA properties can be optimized by changing the composition of the PCCA such as, the crosslinking density, and the PCCA thickness. An increase in the concentration of the photosensitive component results in a stronger response (longer diffraction peak shift). This may require longer exposure time to light, as well as certain wavelengths of UV light. For, example, with 365 nm light, 0.7 mM azobenzene concentration for 80 μm thick PCCA was used.

The preferred range of crosslinking of the hydrogel is between 1% and 5%. Too little crosslinking results in the inability to form the PCCA. Too much crosslinking results in too little photoresponsiveness of the PCCA because the elasticity of the hydrogel is significantly reduced, with the hydrogel being fairly rigid and unable to increase its volume as isomerization occurs.

Thickness of the PCCA can also effect the photoresponsiveness of the photosensitive PCCAs of the present invention. In one embodiment of the present invention, the thickness of the PCCA is preferably in the range from about 10 μm to about 0.5 mm and more preferably in the range from about 40 μm to 80 μm.

The devices of the present invention are useful as optical switch devices, display devices and memory storage devices. The devices of the present invention may be used in the UV, visible or near-infrared region. Photosensitive components resulting in a bigger change in free energy of mixing on photoirradiation may increase the diffraction shift of the devices of the present invention and/or may increase the devices response to illumination by light.

The following examples are intended to illustrate the invention and should not be construed as limiting the invention in any way.

EXAMPLES

Example 1

Free-radical emulsion polymerization was used to synthesize 1H,1H-heptafluorobutyl methacrylate (FBMA) colloidal particles. The polymerization was carried out in a 50-mL three-neck round bottom flask equipped with a reflux condenser, nitrogen inlet, thermometer, and a magnetic stirrer. The flask was immersed in a water bath thermostated at the 50° C. reaction temperature. The reactor was filled with deionized water, Aerosol MA 80-I, and FBMA. The contents were stirred and flushed with nitrogen for about 30 minutes. The initiator ($Na_2S_2O_8$), dissolved in a small amount of water, was then injected into the reactor to start the reaction. The polymerization was carried out under a nitrogen atmosphere for 3 hours.

Highly charged monodisperse colloidal polystyrene particles were formed by emulsion polymerization by→placing approximately 50 g of styrene and about 4 g of 1-sodium-1-allyloxy-2-hydroxypropane sulfonate into about 100 g of water. About 2 g of sodium-di(1,3-dimethylbutyl) sulfosuccinate, about 0.1 g of buffer and about 0.5 g of sodium persulfate dissolved in about 3 ml of water were also added. The mixture was reacted for about 3.5 hours in a flask equipped with a stirring mechanism set at about 350 rpm. The particles were about 105 nm in diameter and were purified by dialysis and ion exchange.

Example 2

A reactive PCCA was made by adding to 3 ml of the CCA medium a mixture comprised of about 0.15 g acrylamide, about 0.005 g N,N'-methylenebisacrylamide, 70 μl glycidyl methacrylate and about 0.01 g of 2,2'-diethoxyacetophenone (UV initiator). The CCA water mixture contained 140 nm fluorinated colloids or polystyrene colloids. These colloids were synthesized by emulsion polymerization from 1H,1H-heptafluorobutyl methacrylate or styrene, respectively (see Example 1). The mixture was injected between two quartz plates (with 80 μm spacing in between the plates) and exposed to UV light (for example, mercury lamp). After 30 minutes, polymerization was completed and the gel was removed from in between the plates and washed with nanopure water.

Example 3

Azobenzene derivative was covalently attached to the PCCA by exposing a previously prepared PCCA to aqueous solution of an azobenzene derivative for 15–30 minutes. This functionalization was done at room temperature, under constant stirring. The exposure time of the gel to the azobenzene derivative solution determined the final concentration of the photochromic molecule inside the PCCA. The azobenzene functionalized gel was washed with nanopure water.

Example 4

Synthesis of Water Soluble Azobenzene Derivative

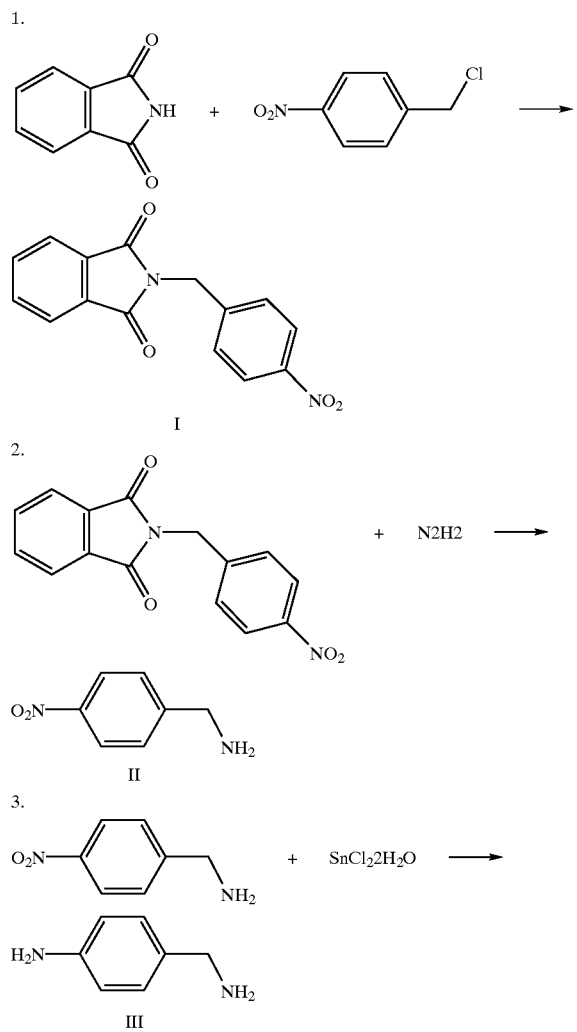

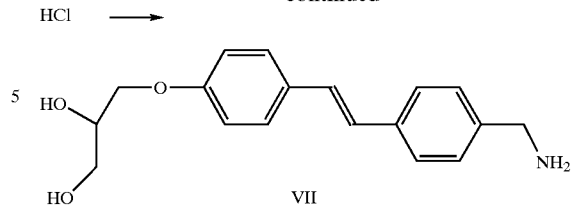

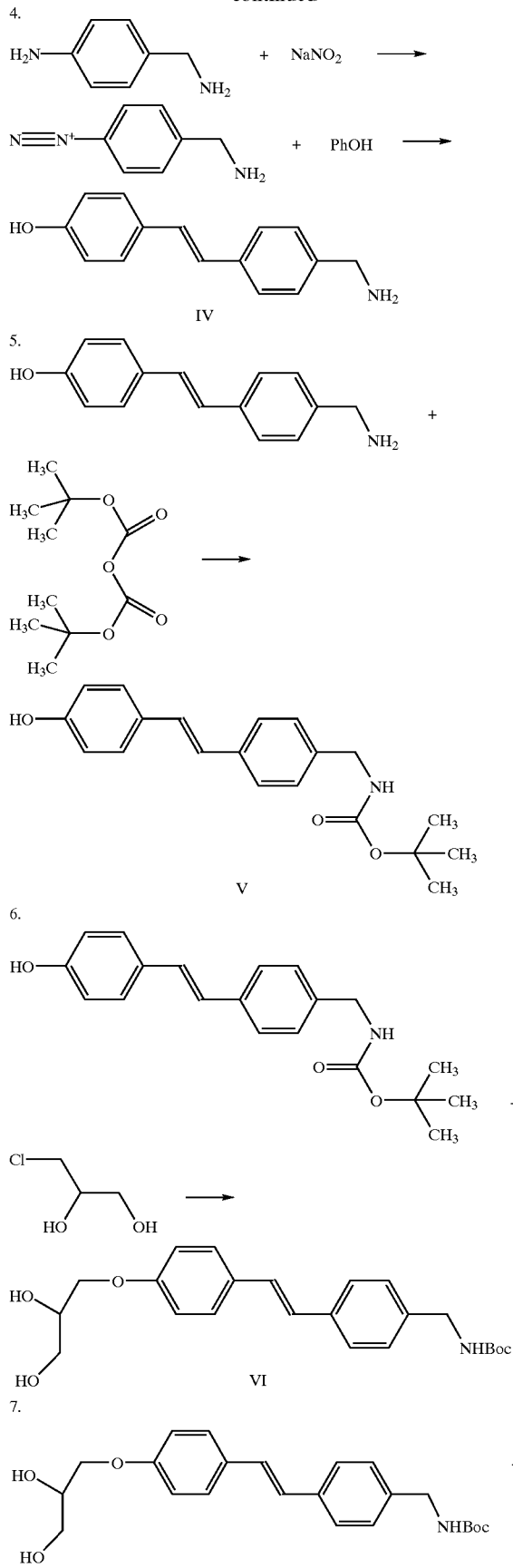

1. N-(p-Nitrobenzyl)-phthalimide (I)

A mixture of phthalimide (4 g), p-nitrophenylmethylchloride (4,7 g), potassium carbonate (4 g) and DMF (20 ml) was stirred at 150° C. for 1.5 h. After cooling, the mixture was diluted with water. The precipitate was filtered and the crude product (I) was recrystallized from ethanol.

MS (EI, 70 eV), m/z (%): 282.0 ($M^+$,90), 265,0 ($M^+$-O), 235,0 ($M^+$-NO)

2. p-Nitrobenzylamine (II)

A mixture of I (7,2 g), hydrazine hydrate (5 g) and ethanol (130 ml) was stirred under reflux for 6 h. After cooling to the room temperature phthalohydrazine was removed by filtration and the solvent was removed in vacuum. The crude compound (II) was used in the next step without further purification.

3. p-Aminobenzylamin (III)

A mixture of (II) (9,1 g), $SnCl_2 2H_2O$ and 36% HCl (120 ml) was stirred under reflux for 1 h. After cooling to 0° C. the precipitate was filtered. The salt ($Cl(H,H_2NPhCH_2NH_2)$ ½$SnCL_6$) was decomposed with KOH and then extracted several times with dichloromethane. The combined organic layers were dried with $Na_2SO_4$. After evaporation of the solvent, the compound (III) was used in the next step without further purification.

4. 4-Aminobenzylazo-phenol (IV)

A freshly prepared solution of $NaNO_2$ (3,46 g) in water (18.3 ml) was added dropwise to a stirred solution of III (6,0 g) in HCl 36% (16 ml) and water (18.6 ml) maintaining the temperature not higher than 5° C. The resulting diazonium salt was added dropwise to a stirred solution of phenol (9,24 g), NaOH (7,86 g) in water (98 ml) at 5° C. The precipitate (compound IV) was filtered, washed with water and dried. Yield 11 g (almost 100%).

MS (EI, 70 eV), m/z (%): 227.0 ($M^+$,80)

5. 4-N-(t-Butoxycarbonyl)-aminomethylbenzolazo-phenol (V)

IV (11 g) was dissolved in dry pyridine (180 ml) at room temperature and then $Boc_2O$ (11,1 g) in dichloromethane (20 ml) was added to the pyridine solution. After 1 h pyridine was removed in vacuum. The residue was purified by column chromatography (silica gel, gradient $CH_2Cl_2$—$CH_2Cl_2$:$CH_3OH$=10:1) to yield the desired compound V. Yield 9 g.

MS (EI, 70 eV), m/z (%): 327.1 ($M^+$,10)

6. 4-N-(t-Butoxycarbonyl)-aminomethylbenzolazo-4-phenoxy glycerol ether (VI)

A mixture of V (3,27 g), potassium carbonate (1,52 g), Cl-glycerine (12 g) was stirred at 100° C. for 13 h. After cooling, the mixture was diluted with water. The precipitate was filtered and the crude compound VI was purified by column chromatography (silica gel, gradient $CH_2Cl_2$:aceton=10:1 to 10:3) to yield the desired compound VI.

Yield 3,5 g.

MS (FD): m/z: 401.0 ($M^+$)

7. 4-N-aminomethylbenzolazo-4-phenoxy glycerol ether (VI)

A mixture of VI (1,7 g) in 160 ml methanol and HCl 36% (8 ml) was stirred at 35° C. for 16 h. After cooling the volume was reduced to 50 ml by removing of the solvent under reduced pressure. Then potassium carbonate (16 g in 20 ml water) and ethanol (100 ml) were added. The precipitate was filtered and the solvent was removed from mother solution in vacuum leaving an orange residue. This was purified by chromatography (silica gel, dichloromethane, methanol and triethylamine 10:2:0.1).

Yield 0.92 g.

$C_{16}H_{19}N_3O_3$ calcd.: C, 63.77, H, 6.36, N, 13.94 (301,34) found: C, 62.3, H, 7.06, N, 13,49

MS (EI, 70 eV), m/z (%): 301.1 (8)($M^+$), 195,0 (3), 166,9(10), 148,9 (3) MS (FD): m/z: 301.3 ($M^+$)

$^{13}$C-NMR (62,9 MHz) $d_6$-DMSO, δ (ppm): 161,6 (C-7), 151,1 (C-1), 146,1 (C-6), 143,3 (C-12), 128,6 (C-2, C-3), 124,5 (C-10, C-11), 122,2 (C-4, C-5), 115,1 (C-8, C-9), 70,1 (C-14), 69,9 (C-15), 62,6 (C-16), 44,0 (C-13)

Whereas particular embodiments of this invention have been described above for purposes of illustration, it will be evident to those skilled in the art that numerous variations of the details of the present invention may be made without departing from the invention as defined in the appended claims.

We claim:

1. A polymerized crystalline colloidal array comprising a photosensitive component, wherein the photosensitive component actuates a volume change in the polymerized crystalline collordal array in response to irradiation.

2. The polymerized crystalline colloidal array of claim 1 wherein said array undergoes a change in volume in response to irradiation.

3. The polymerized crystalline colloidal array of claim 1 wherein said component is a photochromic molecule.

4. The polymerized crystalline colloidal array of claim 3 wherein said photochromic molecule is selected from the group consisting of azobenzenes, spiropyranes, spiroxazines, fulgides, diarylethenes, benzothiazolium styryl dyes, and triphenylmethane derivatives.

5. The polymerized crystalline colloidal array of claim 1 wherein said polymerized crystalline colloidal array is functionalized.

6. The functionalized polymerized crystalline colloidal array of claim 5 wherein said array comprises reactive epoxide groups.

7. The crystalline colloidal array of claim 6 wherein said array is covalently attached to said photosensitive component through the reactive epoxide groups.

8. A polymerized crystalline colloidal array comprising a photochromic molecule.

9. The polymerized crystalline colloidal array of claim 8 wherein said photochromic molecule is selected from the group consisting of azobenzenes, spiropyranes, spiroxazines, fulgides, diarylethenes, benzothiazolium styryl dyes, and triphenylmethane derivatives.

10. A polymerized crystalline colloidal array comprising a photochromic molecule selected from the group consisting of azobenzene, spiropyranes, spiroxazines, fulgides, diarylethenes, benzothiazolium styryl dyes, and triphenylmethane derivatives.

11. A photoresponsive device comprising:
a polymerized crystalline colloidal ordered array of charged particles in a liquid medium; a cell for containing said crystalline colloidal array and medium; and a photosensitive component, wherein said polymerized crystalline colloidal array undergoes a change in volume in response to radiation.

12. The device of claim 11 wherein said photosensitive component is attached to said polymerized crystalline colloidal array.

13. The device of claim 11 wherein said particles are poly(1H,1H-heptafluorobutylmethacrylate) and polystyrene particles.

14. The device of claim 11 wherein said liquid medium is selected from the groups consisting of water, glycerol, ethylene glycol, methanol, ethanol, dimethyl sulfoxide, phenyl methyl sulfoxide, dioxane, dimethylformamide, polyethylene glycol and glycerin.

15. The device of claim 11 wherein said cell is made of a material selected from the group consisting of quartz, a thermoplastic carbonate linked polymer, and glass coated with a thermoplastic carbonate linked polymer.

16. The device of claim 11 wherein said component with photosensitive properties is a photochromic molecule.

17. The device of claim 16 wherein said photochromic molecule is selected from the group consisting of azobenzene, spiropyranes, spiroxazines, fulgides, diarylethenes, benzothiazolium styryl dyes, and triphenylmethane derivatives.

18. The device of claim 11 wherein said device is an optical switch.

19. The device of claim 11 wherein said device is a memory storage device.

20. The device of claim 11 wherein said device is a display device.

21. A radiation tunable device comprising:
a crystalline colloidal ordered array of charged particles polymerized in a hydrogel and a photosensitive component, wherein said hydrogel undergoes a change in volume in response to irradiation.

22. The device of claim 21 wherein said particles are poly(1H,1H-heptafluorobutylmethacrylate) and polystyrene particles.

23. The device of claim 21 wherein said photosensitive component is a photochromic molecule.

24. The device of claim 23 wherein said photochromic molecule is selected from the group consisting of azobenzene, spiropyranes spiroxazines, fulgides, diarylethenes, benzothiazolium styryl dyes, and triphenylmethane derivatives.

25. A thin, two-dimensional display device comprising:
a crystalline colloidal ordered array of charged particles polymerized in hydrogel; a photosensitive component; a means for irradiating said polymerized crystalline colloidal ordered array; and wherein said hydrogel undergoes a change in volume in response to irradiation.

26. The display device of claim 25 wherein said device is useful as a display device in a computer.

27. The display device of claim 25 wherein said display is a monochrome display.

28. The display device of claim 25 wherein said display is a color display.

29. The display device of claim 25 wherein said photosensitive component is a photochromic molecule.

30. The display device of claim 29 wherein said photochromic molecule is selected from the group consisting of azobenzene, spiropyranes, spiroxazines, fulgides, diarylethenes and benzothiazolium styryl dyes, triphenylmethane derivatives.

31. A method of making a photoresponsive device comprising:
placing charged colloidal particles in an aqueous medium in a cell; allowing said charged colloidal particles to self-assemble to form a crystalline colloidal ordered array; polymerizing said charged colloidal particles in a hydrogel to form a functionalized polymerized crystalline colloidal array; attaching a photosensitive component to said functionalized polymerized crystalline colloidal array; and wherein said device undergoes a change in volume in response to irradiation.

32. The method of claim 31, including employing poly(1H,1H-heptafluorobutylmethacrylate) particles as said particles.

33. The method of claim 31 wherein said photosensitive component is a photochromic molecule.

34. The method of claim 33 wherein said photochromic molecule is selected from the group consisting of azobenzene, spiropyranes, spiroxazines, fulgides, diarylethenes, benzothiazolium styryl dyes, and triphenylmethane derivatives.

35. The method of claim 31 wherein said functionalized crystalline colloidal array comprises reactive epoxide groups.

36. The method of claim 31 wherein said functionalized crystalline colloidal array is attached to said photosensitive component through said reactive epoxide groups.

37. A method of making a photosensitive polymerized crystalline colloidal array comprising functionalizing the polymerized crystalline colloidal array and attaching a photosensitive component to the functionalized polymerized crystalline colloidal array, wherein the photosensitive component actuates a volume change in the polymerized crystalline colloidal array in response to irradiation.

38. The method of claim 37 wherein said photosensitive component is a photochromic molecule.

39. The method of claim 37 wherein said photochromic molecule is selected from the group consisting of azobenzene, spiropyranes, spiroxazines, fulgides, diarylethenes, benzothiazolium styryl dyes, and triphenylmethane derivatives.

40. A method of making a photosensitive polymerized crystalline colloidal array comprising copolymerizing glycidyl methacrylate with acrylamide to create a functionalized polymerized crystalline colloidal array with reactive epoxide groups; and incubating said functionalized array with a photosensitive component wherein said component attaches to said functionalized array through said reactive epoxide groups.

41. A composition comprising a crystalline colloidal array of charged particles polymerized in a hydrogel and a photosensitive component wherein said hydrogel undergoes a change in volume in response to irradiation.

42. The composition according to claim 41 wherein said particles are selected from the group consisting of polystyrene, polymethylmethacrylate, silicon dioxide, aluminum oxide, and poly(1H,1H-heptafluorobutylmethacrylate) particles.

43. The composition according to claim 41 further comprising functionalizing the polymerized crystalline colloidal array is by introducing reactive epoxide groups.

44. The composition according to claim 41 wherein said polymerized crystalline colloidal array is covalently attached to said photosensitive component.

45. The composition according to claim 41 wherein the hydrogel is selected from the group consisting of polymer latex, polymethylmethacrylate and polyacrylamide hydrogel.

* * * * *

UNITED STATES PATENT AND TRADEMARK OFFICE
CERTIFICATE OF CORRECTION

PATENT NO. : 6,589,452 B2
DATED : July 8, 2003
INVENTOR(S) : Asher et al.

It is certified that error appears in the above-identified patent and that said Letters Patent is hereby corrected as shown below:

Title page,
Item [56], References Cited, OTHER PUBLICATIONS, "Reese C.E." reference, "*Colloidand*" should read -- *Colloid and* --

Column 1,
Lines 16-17, "phenomena" should read -- phenomenon --

Column 2,
Line 38, "6;" should be deleted

Column 4,
Line 60, "solvents." should read -- solvent. --

Column 5,
Line 15, "$m\lambda. = 2nd \sin \theta;$" should read -- $m\lambda. = 2\ nd \sin \theta;$ --
Line 34, "Highly" should read -- ¶Highly --
Line 49, "by:Reese" should read -- by: Reese --

Column 6,
Line 8, "Bragg diffract" should read -- Bragg-diffracts --
Line 51, "carbodimide" should read -- carbodiimide --
Line 53, "a" should be deleted Column 9,
Line 19, "as" should read -- to --
Line 48, "due to the point" should read -- due to the fact that the point --

Column 11,
Line 7, "N2H2" should read -- $N_2H_2$ --

Column 13,
Line 17, "effect" should read -- affect --
Line 52, "by→placing" should read -- by placing --

Column 14,
Line 47, "N2H2" should read -- $N_2H_2$ --

UNITED STATES PATENT AND TRADEMARK OFFICE
CERTIFICATE OF CORRECTION

PATENT NO. : 6,589,452 B2
DATED : July 8, 2003
INVENTOR(S) : Asher et al.

It is certified that error appears in the above-identified patent and that said Letters Patent is hereby corrected as shown below:

Column 16,
Line 14, "(4,7 g)" should read -- (4.7 g) --
Line 19, "265,0" should read -- 265.0 --
Line 20, "235,0" should read -- 235.0 --
Line 24, "(7,2 g)" should read -- (7.2 g) --
Line 32, "(9,1 g)" should read -- (9.1 g) --
Line 42, "(3,46 g)" should read -- (3.46 g) --
Line 43, "(6,0" should read -- (6.2 --
Line 46, "(9,24" should read -- (9.24 --
Line 47, "(7,86 g)" should read -- (7.86 g) --
Line 55, "(11,1 g)" should read -- (11.1 g) --
Line 58, "$CH_2Cl_2$—" should read -- $CH_2Cl_2$- --
Line 66, "(3,27 g)" should read -- (3.27 g) --; and "(1,52 g)" should read -- (1.52 g) --

Column 17,
Line 4, "aceton" should read -- acetone --
Line 10, "(1,7)" should read -- (1.7) --
Line 20, "(301,34)" should read -- (301.34) --
Line 21, "13,49" should read -- 13.49 --
Line 22, "195,0" should read -- 195.0 --
Line 23, "166,9" should read -- 166.9 --; and "148,9" should read -- 148.9 --
Line 24, "(62,9" should read -- (62.9 --; and "161,6" should read -- 161.6 --
Line 25, "151,1" should read -- 151.1 --; "146,1" should read -- 146.1 --; "143,3" should read -- 143.3 --; and "128,6" should read -- 128.6 --
Line 26, "124,5" should read -- 124.5 --; "122,2" should read -- 122.2 --; "115,1" should read -- 115.1 --; and "70,1" should read -- 70.1 --
Line 27, "69,9" should read -- 69.9 --; "62,6" should read -- 62.6 --; and "44,0" should read -- 44.0 --
Line 39, "collordal" should read -- colloidal --

Column 18,
Line 50, "sproipyranes spiroxazines," should read -- spiropyranes, spiroxazines, --

UNITED STATES PATENT AND TRADEMARK OFFICE
CERTIFICATE OF CORRECTION

PATENT NO. : 6,589,452 B2
DATED : July 8, 2003
INVENTOR(S) : Asher et al.

It is certified that error appears in the above-identified patent and that said Letters Patent is hereby corrected as shown below:

<u>Column 20,</u>
Line 28, "is" should be deleted

Signed and Sealed this

First Day of June, 2004

JON W. DUDAS
*Acting Director of the United States Patent and Trademark Office*